(12) United States Patent
Choi-Sledeski et al.

(10) Patent No.: US 8,710,080 B2
(45) Date of Patent: Apr. 29, 2014

(54) PRODRUGS OF [4 [4-(5-AMINOMETHYL-2-FLUORO-PHENYL)-PIPERIDIN-1-YL]-(1H-PYRROLO-PYRIDIN-YL)-METHANONES AND SYNTHESIS THEREOF

(75) Inventors: Yong Mi Choi-Sledeski, Belle Mead, NJ (US); Gregory B. Poli, Bethlehem, PA (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/488,533

(22) Filed: Jun. 5, 2012

(65) Prior Publication Data

US 2012/0238573 A1    Sep. 20, 2012

Related U.S. Application Data

(63) Continuation of application No. PCT/US2010/061434, filed on Dec. 21, 2010.

(60) Provisional application No. 61/289,537, filed on Dec. 23, 2009.

(30) Foreign Application Priority Data

Sep. 10, 2010    (FR) ...................... 10 57197

(51) Int. Cl.
*A61K 31/404* (2006.01)
*C07D 401/08* (2006.01)

(52) U.S. Cl.
USPC ......................................... 514/323; 546/201

(58) Field of Classification Search
USPC ....................................................... 546/201
See application file for complete search history.

(56) References Cited

U.S. PATENT DOCUMENTS 6,977,263 B2    12/2005    Astles et al.

FOREIGN PATENT DOCUMENTS

| WO | WO 01/90101 A1 | 11/2001 |
| WO | WO 2010/022196 A2 | 2/2010 |
| WO | WO 2011/079095 A1 | 6/2011 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Testa. Biochemical Pharmacology 68 (2004) 2097-2106.*
McEuen, et al., Guinea Pig Lung Tryptase, Biochemical Pharmacology, vol. 52, pp. 331-340, (1996).
Liang, et al., A Conformationally Constrained Inhibitor With an Enhanced Potency for B-Tryptase and Stability Against Semicarbazide-Sensitive Amine Oxidase (SSAO), Bioorganic & Medicicnal Chemistry Letters, vol. 20, (2010), pp. 6721-6724.

* cited by examiner

*Primary Examiner* — Shawquia Young
(74) *Attorney, Agent, or Firm* — Ronald G. Ort

(57) ABSTRACT

The present invention relates to substituted 2-amino-N-(4-fluoro-3-{1-[1-(alkyl)-1H-indole-3-carbonyl]-piperidin-4-yl}-benzyl)-acetamides (compounds of formula I)

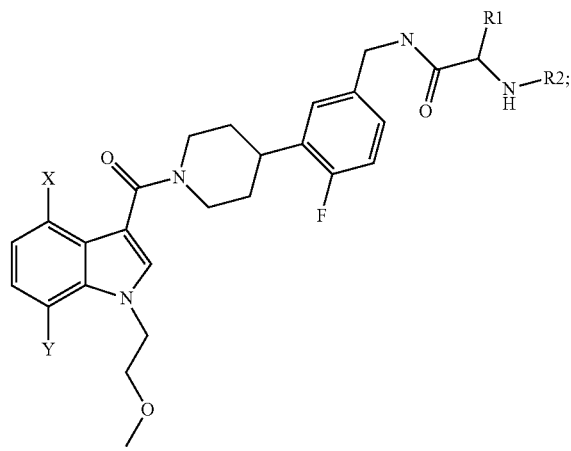

compositions thereof, and their use in the treatment of inflammatory diseases.

7 Claims, No Drawings

PRODRUGS OF [4 [4-(5-AMINOMETHYL-2-FLUORO-PHENYL)-PIPERIDIN-1-YL]-(1H-PYRROLO-PYRIDIN-YL)-METHANONES AND SYNTHESIS THEREOF

FIELD OF THE INVENTION

Provided herein are novel and useful compounds having tryptase inhibition activity in their prodrug form and the intermediates thereof, pharmaceutical compositions comprising such compounds, and a method of treating subjects suffering from a condition disease or disorder that can be ameliorated by the administration of an inhibitor of tryptase including but not limited to for example asthma and other inflammatory diseases.

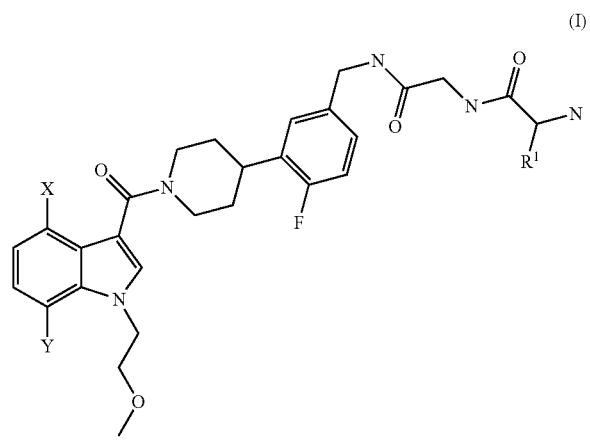

(I)

BACKGROUND OF THE INVENTION

Mast cell mediated inflammatory conditions, in particular asthma, are a growing public health concern. Asthma is frequently characterized by progressive development of hyperresponsiveness of the trachea and bronchi to both immunospecific allergens and generalized chemical or physical stimuli, which lead to the onset of chronic inflammation. Leukocytes containing IgE receptors, notably mast cells and basophils, are present in the epithelium and underlying smooth muscle tissues of bronchi. These leukocytes initially become activated by the binding of specific inhaled antigens to the IgE receptors and then release a number of chemical mediators. For example, degranulation of mast cells leads to the release of proteoglycans, peroxidase, arylsulfatase B, chymase, and tryptase, which results in bronchiole constriction.

Tryptase is stored in the mast cell secretory granules and is the major secretory protease of human mast cells. Tryptase has been implicated in a variety of biological processes, including degradation of vasodilating and bronchorelaxing neuropeptides (Caughey, et al., J. Pharmacol. Exp. Ther., 1988, 244, pages 133-137; Franconi, et al., J. Pharmacol. Exp. Ther., 1988, 248, pages 947-951; and Tam, et al., Am. J. Respir. Cell Mol. Biol., 1990, 3, pages 27-32) and modulation of bronchial responsiveness to histamine (Sekizawa, et al., J. Clin. Invest., 1989, 83, pages 175-179).

As a result, tryptase inhibitors may be useful as anti-inflammatory agents (K Rice, P. A. Sprengler, Current Opinion in Drug Discovery and Development, 1999, 2(5), pages 463-474) particularly in the treatment of chronic asthma (M. Q. Zhang, H. Timrnerman, Mediators Inflarnm., 1997, 112, pages 311-317), and may also be useful in treating or preventing allergic rhinitis (S. J. Wilson et al, Clin. Exp. Allergy, 1998, 28, pages 220-227), inflammatory bowel disease (S. C. Bischoff et al, Histopathology, 1996, 28, pages 1-13), psoriasis (A. Naukkarinen et al, Arch. Dermatol. Res., 1993, 285, pages 341-346), conjunctivitis (A. A. Irani et al, J. Allergy Clin. Immunol., 1990, 86, pages 34-40), atopic dermatitis (A. Jarvikallio et al, Br. J. Dermatol., 1997, 136, pages 871-877), rheumatoid arthritis (L. C Tetlow et al, Ann. Rheum. Dis., 1998, 54, pages 549-555), osteoarthritis (M. G. Buckley et al, J. Pathol., 1998, 186, pages 67-74), gouty arthritis, rheumatoid spondylitis, and diseases of joint cartilage destruction. In addition, tryptase has been shown to be a potent mitogen for fibroblasts, suggesting its involvement in pulmonary fibrosis in asthma and interstitial lung diseases (Ruoss et al., J. Clin. Invest., 1991, 88, pages 493-499). Therefore, tryptase inhibitors may be useful in treating or preventing fibrotic conditions (J. A. Cairns and A. F. Walls, J. Clin. Invest., 1997, 99, pages 1313-1321) for example, fibrosis, sceleroderma, pulmonary fibrosis, liver cirrhosis, myocardial fibrosis, neurofibromas and hypertrophic scars.

Additionally, tryptase inhibitors may be useful in treating or preventing myocardial infarction, stroke, angina and other consequences of atherosclerotic plaque rupture (M. Jeziorska et al, J. Pathol., 1997, 182, pages 115-122).

Tryptase has also been discovered to activate prostromelysin that in turn activates collagenase, thereby initiating the destruction of cartilage and periodontal connective tissue, respectively.

Therefore, tryptase inhibitors could be useful in the treatment or prevention of arthritis, periodontal disease, diabetic retinopathy, and tumor growth (W. J. Beil et al, Exp. Hematol., (1998) 26, pages 158-169). Also, tryptase inhibitors may be useful in the treatment of anaphylaxis (L. B. Schwarz et al, J. Clin. Invest., 1995, 96, pages 2702-2710), multiple sclerosis (M. Steinhoff et al, Nat. Med. (N.Y.), 2000, 6(2), pages 151-158), peptic ulcers and syncytial viral infections.

U.S. Pat. No. 6,977,263 discloses compounds including [(benzylamine)-piperidin-1-yl] (aryl or heteroaryl)methanone as tryptase inhibitors, and describes potential uses for such compounds due to tryptase being implicated in a variety of biological processes, including degradation of vasodilating and bronchorelaxing neuropeptides (Caughey, et al., J. Pharmacol. Exp. Ther., 1988, 244, pages 133, 137; Franconi, et al., J. Pharmacol. Exp. Ther., 1988, 248, pages 947-951; and Tam, et al., Am. J. Respir. Cell Mol. Biol., 1990, 3, pages 27-32) and modulation of bronchial responsiveness to histamine (Sekizawa, et al., J. Clin. Invest., 1989, 83, pages 175-179).

U.S. Pat. No. 6,977,263 more particularly discloses the compounds of formula A, their preparation, and use for treating disease states capable of being modulated by the inhibition

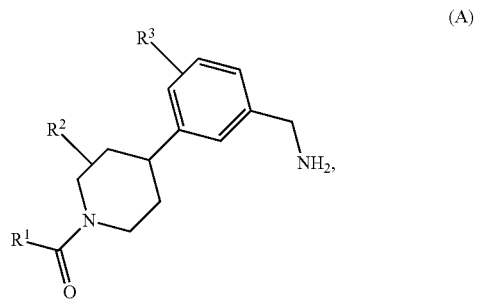

(A)

of tryptase. U.S. Pat. No. 6,977,263 also discloses that R[1] of formula A may be an aryl or heteroaryl group. Heteroaryl groups that are exemplified in the U.S. Pat. No. 6,977,263 are alkylpyridyl, alkylthienyl, and indoyl.

Accordingly, what is needed is a novel and useful compound having particularly valuable pharmaceutical properties, in its ability to inhibit tryptase and be readily bioavailable. Such a compound should readily have utility in treating a patient suffering from conditions that can be ameliorated by the administration of an inhibitor of tryptase, e.g., mast cell mediated inflammatory conditions, inflammation, and diseases or disorders related to the degradation of vasodilating and bronchorelaxing neuropeptides.

The present invention further relates to a method for treating or ameliorating macular degeneration in a patient.

Macular degeneration is the general term for a disorder in which a part of the retina called the macula deteriorates. Age-related macular degeneration (AMD) is the most common type of macular degeneration. It has been reported that in the United States, AMD is the leading cause of blindness in people older than 55. More than 10 million people in the US are affected by this disease, which includes 23% of people over 90. (www.webmd.com/eye-health/macular-degeneration/macular-degeneration-overview).

There are various types of macular degeneration that afflict patients. One type of macular degeneration is "dry" macular degeneration. Dry macular degeneration is an early stage of the disorder in which a pigment is deposited on the macula. The deposition of this pigment may result from aging or thinning of the macular tissues. As a result of this deposition of pigment, loss of central vision may gradually occur. Many times, AMD begins with dry macular degeneration.

Another type of AMD is "wet" macular degeneration. Wet macular degeneration is a neovascular type of degeneration in which blood vessels abnormally grow under the retina and begin to leak. As a result of this leakage, permanent damage occurs to light-sensitive cells of the retina which ultimate causes the death of these cells and thus, blind spots. Unlike dry macular degeneration, in which the vision loss may be minor, the vision loss that occurs in wet macular degeneration can be severe. Indeed, it has been reported that although only 10% of those with AMD suffer from wet macular degeneration, 66% of those with AMD suffering from significant visual loss can directly attribute that loss to wet macular degeneration.

Since the causes for macular degeneration are unknown, there has only be limited success determining the causes for the disorder. Moreover, treatments for macular degeneration have met with only limited limited success. To date, there is no FDA-approved treatment for dry macular degeneration and nutritional intervention is used to prevent the progression of wet macular degeneration.

Furthermore, in a method of the present invention, administration of a compound to the patient suffering from macular degeneration modulates the activity of an immunocyte in the patient. The activity of numerous types of immunocytes can be modulated in a method of the present invention. Examples of such immunocytes include a natural killer cell (NK cell), a natural killer T cell (NKT cell), a mast cell, a dendritic cell, and granulocyte selected from the group consisting of an eosinophil, a basophil and neutrophil. Naturally, the activity of a combination of these cells can also be modulated in a method of the present invention.

Moreover, a method of the present invention can also be used to treat or ameliorate choroidal neovascularization, which in turn also treats or ameliorates wet macular degeneration in the patient.

Accordingly, the present invention relates to a method of treating a patient in need of amelioration of AMD with a compound of Formula I.

SUMMARY OF THE INVENTION

The present invention is directed to substituted 2-amino-N-(4-fluoro-3-{1-[1-(alkyl)-1H-indole-3-carbonyl]-piperidin-4-yl}-benzyl)-acetamides (compounds of formula I)

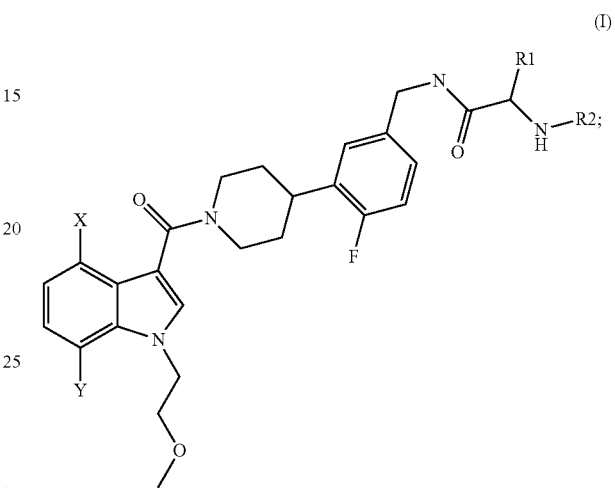

to the syntheses of said compounds and or a prodrug, pharmaceutically acceptable salt, or solvate of said compound to a method of treating patients in need there of. Furthermore, the present invention is directed to a pharmaceutical composition comprising a pharmaceutically effective amount of the compound of formula I, and a pharmaceutically acceptable carrier. Furthermore, the present invention is directed to the use of a compound of formula I as a prodrug of a tryptase inhibitor comprising introducing the compound into a composition comprising tryptase. In addition, the present invention is directed to the use of a compound of formula I for treating a patient suffering from, or subject to, a physiological condition in need of amelioration of an inhibitor of tryptase comprising administering to the patient a therapeutically effective amount of the compound of claim 1. The present invention is directed also to the preparation of a compound of formula I.

DETAILED DESCRIPTION

Definitions

As used above, and throughout the instant specification and appending claims, the following terms, unless otherwise indicated, shall be understood to have the following meanings:

As used herein, the term "compound of the present invention", and equivalent expressions, are meant to embrace the compound of formula I, as hereinbefore described, which expression includes the prodrug, the pharmaceutically acceptable salt and the solvate, e.g., hydrate. Similarly, reference to intermediates, whether or not they themselves are claimed, is meant to embrace the salts, and solvates, where the context so permits. For the sake of clarity, particular instances when the context so permits are sometimes indicated in the text, but these instances are purely illustrative and they are not intended to exclude other instances when the context so permits.

As used herein, the term "treatment" or "treating" includes prophylactic therapy as well as treatment of an established condition.

"Patient" means a human or other mammal.

"Effective amount" is meant to describe an amount of a compound effective in producing the desired therapeutic effect.

"Prodrug" means a compound that is suitable for administration to a patient without undue toxicity, irritation, allergic response, and the like, and is convertible in vivo by metabolic means (e.g. by hydrolysis) to the compound of the present invention. A thorough discussion of prodrugs is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

Particular Embodiments

In addition, the present invention is directed to the use of the compound of formula I for treating a patient suffering from a physiological condition that can be ameliorated by administering to the patient a therapeutically effective amount of the compound of formula I. Particular embodiments of physiological conditions that can be treated with the compound of the present invention include, but certainly are not limited to inflammatory diseases, e.g., joint inflammation, arthritis, rheumatoid arthritis, rheumatoid spondylitis, gouty arthritis, traumatic arthritis, rubella arthritis, psoriatic arthritis, and other chronic inflammatory joint diseases. Other embodiments of physiological conditions that can be treated by the present invention include physiological conditions such as chronic obstructive pulmonary disease (COPD), COPD exacerbations, joint cartilage destruction, ocular conjunctivitis, vernal conjunctivitis, inflammatory bowel disease, asthma, allergic rhinitis, interstitial lung diseases, fibrosis, sceleroderma, pulmonary fibrosis, acute macular degeneration, macular degeneration, wet macular degeneration, liver cirrhosis, myocardial fibrosis, neurofibromas, hypertrophic scars, various dermatological conditions, for example, atopic dermatitis and psoriasis, myocardial infarction, stroke, angina and other consequences of atherosclerotic plaque rupture, as well as periodontal disease, diabetic retinopathy, tumor growth, anaphylaxis, multiple sclerosis, peptic ulcers, and syncytial viral infections.

In a particular embodiment, the present invention is directed to the use of a compound of formula I for treating a patient suffering from asthma, comprising administering to the patient a physiologically effective amount of the compound.

In another particular embodiment, the present invention is directed to the use of a compound of formula I for treating a patient suffering from COPD, comprising administering to the patient a physiologically effective amount of the compound.

In another particular embodiment, the present invention is directed to the use of a compound of formula I for treating a patient suffering from COPD exacerbations, comprising administering to the patient a physiologically effective amount of the compound.

In another particular embodiment, the present invention is directed to the use of a compound of formula I for treating a patient suffering from allergic rhinitis, comprising administering to the patient a physiologically effective amount of the compound.

In another particular embodiment, the present invention is directed to the use of a compound of formula I for treating a patient suffering from joint inflammation, comprising administering to the patient a physiologically effective amount of the compound.

In another particular embodiment, the present invention is directed to the use of a compound of formula I for treating a patient suffering from macular degeneration, comprising administering to the patient a physiologically effective amount of the compound.

In another particular embodiment, the present invention is directed to the use of a compound of formula I for treating a patient suffering from wet macular degeneration, comprising administering to the patient a physiologically effective amount of the compound.

In another particular embodiment, the present invention is directed to the use of a compound of formula I for treating a patient suffering from acute macular degeneration, comprising administering to the patient a physiologically effective amount of the compound.

In addition, the present invention extends to a pharmaceutical composition comprising the compound of formula I, a second compound selected from the group consisting of a beta adrenergic agonist, an anticholinergic, an anti-inflammatory corticosteroid, and an anti-inflammatory agent, and a pharmaceutically acceptable carrier thereof. In such a composition the compound of formula I and the second compound are present in amounts such that provide a therapeutically efficacious activity, i.e., additive or synergistic effect. Particular inflammatory diseases or disorders that can be treated with such a pharmaceutical composition include, but is not limited to, asthma.

Moreover, the present invention is directed to a method for treating a patient suffering from an inflammatory disorder, comprising administering to the patient the compound of formula I and a second compound selected from the group consisting of a beta adrenergic agonist, an anticholinergic, an anti-inflammatory corticosteroid, and an anti-inflammatory agent. In such a method, the compound of formula I and the second compound are present in amounts such that provide a therapeutically efficacious activity, i.e., additive or synergistic effect. In such a method of the present invention, the compound of the present invention can be administered to the patient before a second compound, a second compound can be administered to the patient before a compound of the present invention, or a compound of the present invention and a second compound can be administered concurrently. Particular examples of adrenergic agonists, anticholinergics, anti-inflammatory corticosteroids, and anti-inflammatory agents having application according to the method are described infra.

Pharmaceutical Compositions

As explained above, the compound of the present invention exhibits useful pharmacological activity and accordingly may be incorporated into a pharmaceutical composition and used in the treatment of patients suffering from certain medical disorders. The present invention thus provides, according to a further aspect, pharmaceutical compositions comprising the compound of the invention, and a pharmaceutically acceptable carrier thereof. As used herein, the term "pharmaceutically acceptable" preferably means approved by a regulatory agency of a government, in particular the Federal government or a state government, or listed in the U.S. Pharmacopoeia or another generally recognized pharmacopoeia for use in animals, and more particularly in humans. Suitable pharmaceutical carriers are described in "Remington's Pharmaceutical Sciences" by E. W. Martin. Pharmaceutical compositions according to the present invention can be prepared according to the customary methods, using one or more pharmaceutically acceptable adjuvants or excipients. The adjuvants comprise, inter alia, diluents, fillers, binders, disintegrants, glidants, lubricants, surfactants, sterile aqueous media and the various non-toxic organic solvents. The composite oils may be presented in the form of tablets, capsules, pills, sustained release formulations, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, microcrystalline cellulose, pregelatinized starch, unmodified starch, silicified microcrystalline cellulose, mannitol, sorbitol, xylitol, dextrates, fructose, sodium citrate, calcium carbonate, dicalcium phosphate dihydrate, anhydrous dicalcium phosphate, calcium sulfate, along with binders such as polyvinylpyrollidone, hydroxypropylmethyl cellulose, ethyl cellulose, hydroxyethyl cellulose, methyl cellulose, sodium carboxymethyl cellulose, pregelatinized starch, starch, polyethylene glycols, polyethylene oxide, polycarbophils, gelatin and acacia and disintegrating agents such as sodium croscannellose, sodium starch glycolate, crospovidone, starch, microcrystalline cellulose, alginic acids and certain complex silicates combined with lubricants such as magnesium stearate, calcium stearate, stearic acid, hydrogenated vegetable oil, mineral oil, polyethylene glycols, glyceryl esters of fatty acids, sodium lauryl sulfate and glidants such as silicon dioxide, talc, starch, along with some suitable wetting agent such as sodium lauryl sulfate, sorbitan esters, polyoxyethylene fatty acid esters, poloxamer, polyoxyethylene ether, sodium docusate, polyethoxylated castor oil, and benzalkonium chloride may be used for preparing tablets. To prepare a capsule, it is advantageous to use fillers such as lactose, microcrystalline cellulose, pregelatinized starch, unmodified starch, silicified microcrystalline cellulose alone or a mixture of two or more fillers, with and without binders as described above along with suitable wetting agent (s), disintegrants, glidants, lubricants, etc. as listed above. When aqueous suspensions are used they can contain emulsifying agents or agents which facilitate suspension.

Diluents such as sucrose, ethanol, polyethylene glycol, propylene glycol, glycerol and chloroform or mixtures thereof may also be used. Such pharmaceutically acceptable carriers can also be sterile water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include mannitol, human serum albumin (HSA), starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

Naturally, a pharmaceutical composition of the present invention will contain a therapeutically effective amount of the active compound together with a suitable amount of carrier so as to provide the form for proper administration to the patient. While intravenous injection is a very effective form of administration, other modes can be employed, such as by injection, or by oral, nasal or parenteral administration, which are discussed infra.

Methods of Treatment

The compound of formula I possesses tryptase inhibition activity according to tests described in the literature and described hereinafter, and which test results are believed to correlate to pharmacological activity in humans and other mammals. In addition the compound in formula one is a prodrug of a compound that possesses in-vitro tryptase activity according to test described in the literature. Thus, in a further embodiment, the present invention is directed to the use of formula I or a composition comprising it for treating a patient suffering from, or subject to, a condition that can be ameliorated by the administration of an inhibitor of tryptase. For example, the compound of formula I is useful for treating an inflammatory disease, for example, joint inflammation, including arthritis, rheumatoid arthritis and other arthritic condition such as rheumatoid spondylitis, gouty arthritis, traumatic arthritis, rubella arthritis, psoriatic arthritis, osteoarthritis or other chronic inflammatory joint disease, or diseases of joint cartilage destruction, ocular conjunctivitis, vernal conjunctivitis, inflammatory bowel disease, asthma, allergic rhinitis, interstitial lung diseases, fibrosis, scleroderma, pulmonary fibrosis, liver cirrhosis, myocardial fibrosis, neurofibromas, hypertrophic scars, various dermatological conditions, for example, atopic dermatitis and psoriasis, myocardial infarction, stroke, angina or other consequences of atherosclerotic plaque rupture, as well as periodontal disease, diabetic retinopathy, macular degeneration, acute macular degeneration, wet, macular degeneration, tumor growth, anaphylaxis, multiple sclerosis, peptic ulcers, or a syncytial viral infection.

According to a further feature of the invention there is provided a method for the treatment of a human or animal patient suffering from, or subject to, conditions which can be ameliorated by the administration of an inhibitor of tryptase, for example conditions as hereinbefore described, which comprises the administration to the patient of an effective amount of compound of the invention or a composition containing a compound of the invention.

Combination Therapy

As explained above, other pharmaceutically active agents can be employed in combination with the compound of formula I depending upon the disease being treated. For example, in the treatment of asthma, beta-adrenergic agonists such as albuterol, terbutaline, formoterol, fenoterol or prenaline can be included, as can anticholinergics such as ipratropium bromide, anti-inflammatory corticosteroids such as beclomethasone dipropionate, triamcinolone acetonide, flunisolide or dexamethasone, and anti-inflammatory agents such as sodium cromoglycate and nedocromil sodium. Thus, the present invention extends to a pharmaceutical composition comprising the compound of formula I and a second compound selected from the group consisting of a beta adrenergic agonist, an anticholinergic, an anti-inflammatory corticosteroid, and an anti-inflammatory agent; and a pharmaceutically acceptable carrier thereof. Particular pharmaceutical carriers having applications in this pharmaceutical composition are described herein.

Furthermore, the present invention extends to a method for treating a patient suffering from asthma, comprising administering the patient the compound of the present invention, and a second compound selected from the group consisting of a beta adrenergic agonist, an anticholinergic, an anti-inflammatory corticosteroid, and an anti-inflammatory agent. In such a combination method, the compound of the present invention can be administered prior to the administration of the second compound, the compound of the present invention can be administered after administration of the second compound, or the compound of the present invention and the second compound can be administered concurrently.

Modes of Delivery

According to the invention, the compound of formula I, or a pharmaceutical composition comprising the compound, may be introduced parenterally, transmucosally, e.g., orally, nasally, intraocularly, pulmonarily, or rectally, or transdermally to a patient.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for a therapeutic is given by Marshall, K. In: Modern Pharmaceutics Edited by G. S. Banker and C. T. Rhodes Chapter 10, 1979, herein incorporated by reference. In general, the formulation will include a compound of the present invention, and inert ingredients that allow for protection against the stomach environment, and release of the biologically active material, i.e., a compound of the present invention, in the intestine.

Also specifically contemplated are oral dosage forms of the compound of the present invention. Such a compound may be chemically modified so that oral delivery is more efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the compound of the present invention, and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the compound of the present invention, the location of release may be the stomach, the small intestine (the duodenum, the jejunum, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the compound of the present invention, or by release of the compound beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings. can also be used on tablets, which are not intended for protection against the stomach. This can include sugar coatings, or coatings that make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the present invention may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, alpha-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to starch, including the commercial disintegrant based on starch, Explotab sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of a compound of the present invention either alone or as a mixture in different ratios.

Additives that potentially enhance uptake of the compound of the present invention are, for instance, the fatty acids oleic acid, linoleic acid and linolenic acid. Controlled release oral formulation may be desirable. The drug could be incorporated into an inert matrix that permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars that could be applied in a coating pan. The therapeutic agent could also be given in a film-coated tablet and the materials used in this instance are divided into 2 groups. The first are the non-enteric materials and include methyl cellulose, ethyl cellulose, hydroxyethyl cellulose, methylhydroxyethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Pulmonary Delivery

Also contemplated herein is pulmonary delivery of the compound of the present invention, either alone, or in a pharmaceutical composition. The compound is delivered to the lungs of a mammal while inhaling and traverses across the lung epithelial lining to the blood stream. Other reports of this include Adjei et al., 1990, Pharmaceutical Research, 7:565-569; Adjei et al., 1990, International Journal of Pharmaceutics, 63: 135-144 (leuprolide acetate); Braquet et al., 1989, Journal of Cardiovascular Pharmacology, 13 (suppl. 5): 143-146 (endothelin-1); Hubbard et al., 1989, Annals of Internal Medicine, Vol. III, pp. 206-212 (al-antitrypsin); Smith et al., 1989, J. Clin. Invest. 84: 1145-1146 (a-1-proteinase); Oswein et al., 1990, "Aerosolization of Proteins", Proceedings of Symposium on Respiratory Drug Delivery 11, Keystone, Colo., March, (recombinant human growth hormone); Debs et al., 1988, J. Immunol. 140:3482-3488 (interferon-γ and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Wallinckrodt, Inc., St. Louis, Mo.; the Acorn I1 nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass., to name only a few. All such devices require the use of formulations suitable for the dispensing of the compound of the present invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. A chemically modified compound of the present invention may also be prepared in different formulations depending on the type of chemical modification or the type of device employed.

Formulations suitable for use with a nebulizer, either jet or ultrasonic, will typically comprise the compound of the present invention dissolved in water at a concentration of about 0.1 to 25 mg of compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound of the invention suspended in a propellant with the aid of a surfactant. The propellant may be any conventional material employed for this purpose, such as a chlorofluorocarbon, hydrochlorofluorocarbon, hydrofluorocarbon, a r hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the compound of the invention, and may also include a bulking agent, such as lactose, sorbitol, sucrose, or mannitol in amounts which facilitate dispersal of the powder from the device, e.g., 50 to 90% by weight of the formulation. The compound of the present invention should most advantageously be prepared in particulate form with an average particle size of less than 10 mm (or microns), most preferably 0.5 to 5 mm, for most effective delivery to the distal lung.

Nasal Delivery

Nasal delivery of the compound of the present invention is also contemplated. Nasal delivery allows the passage of the compound to the blood stream directly after administering the therapeutic product to the nose, without the necessity for deposition of the product in the lung. Formulations for nasal delivery include those with dextran or cyclodextran.

Intraocular Delivery

Intraocular delivery of the compound of the present invention is also contemplated. Various and numerous methods are known in the art for intraoculal administration of a drug. Intraocular delivery allows the passage of the compound to the intraocular fluid directly after administering the therapeutic product to the eye, without the necessity for oral administration of the product. Formulations for intraocular delivery may include, but are not limited to, solutions or suspensions in aqueous or non-aqueous media.

Transdermal Delivery

Various and numerous methods are known in the art for transdermal administration of a drug, e.g., via a transdermal patch. Transderma administration methods have applications in the present invention. Transdermal patches are described in for example, U.S. Pat. No. 5,407,713, issued Apr. 8, 1995 to Rolando et al.; U.S. Pat. No. 5,352,456, issued Oct. 4, 1994 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Topical Administration

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

Rectal Administration

Solid compositions for rectal administration include suppositories formulated in accordance with known methods and containing the compound of the invention.

Dosages

The percentage of active ingredient in the composition of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg per kg body weight per day by inhalation, from about 0.01 to about 100, preferably 0.1 to 70, more especially 0.5 to 10, mg per kg body weight per day by oral administration, and from about 0.001 to about 10, preferably 0.01 to 1, mg per kg body weight per day by intravenous administration. In each particular case, the doses will be determined in accordance with the factors distinctive to the subject to be treated, such as age, weight, general state of health and other characteristics which can influence the efficacy of the medicinal product.

Furthermore, the compound according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Naturally, a patient in whom administration of the compound of the present invention is an effective therapeutic regimen is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Preparatory Details

The compound of formula I may be prepared by the application or adaptation of known methods, by which is meant methods used heretofore or described in the literature, for example those described by R. C. Larock in Comprehensive Organic Transformations, VCH publishers, 1989, or as described herein.

In the reactions described hereinafter it may be necessary to protect reactive functional groups, for example, amino groups, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991. In particular, the compound of formula I may be prepared as shown through Examples 1-20 below. For example, the compound of the present invention is a chiral prodrug whose preparation is comprised of a convergent synthesis.

As used throughout the specification, the following abbreviations and definitions, unless otherwise indicated, shall be understood to have the following meanings:

LIST OF ABBREVIATIONS

APCI atmospheric pressure chemical ionization
BOC tert-butyl dicarbonate
BOC anhydride di-tert-butyl dicarbonyl anhydride
t-Bu tert-butyl
t-BuOH tert-butanol
$CDCl_3$ deuterated chloroform
$CD_3OD$ deuterated methanol
DCM dichloromethane, $CH_2Cl_2$ or methylenechloride
DMAP 4-dimethylaminopyridine
DMF dimethylformamide
DMSO dimethylsulfoxide
DMSO-$d_6$ dimethyl-d6 sulfoxide
dppf 1,1'-bis(diphenylphosphino)ferrocene
eq equivalent(s)
Et ethyl
$Et_2O$ diethyl ether
$Et_3N$ triethylamine
EtOH ethanol
EtOAc ethyl acetate
EDCI 1-ethyl-3-(3'-dimethylaminopropyl)carbodiimide
HPLC high performance liquid chromatography
$H_2$ hydrogen
L Liter
LC/MS liquid chromatography-mass spectrometry
M molar
Me methyl
MeCN acetonitrile MeOH methanol
MgSO$_4$ magnesium sulfate
MHz megahertz
min minute
OMe methoxide
NaHCO$_3$ sodium bicarbonate
Na$_2$CO$_3$ sodium carbonate
NaCl sodium chloride
NaOH sodium hydroxide
NaI sodium iodide
NaOMe sodium methoxide
Na$_2$SO$_4$ sodium sulfate
n-BuOAc n-butyl acetate
NMR nuclear magnetic resonance
Pd/C Palladium on carbon
Pd(PPh$_3$)$_4$ tetrakistriphenylphosphine palladium
Pd(PPh$_3$)$_2$Cl$_2$ bistriphenylphosphine palladium (II) dichloride
PdCl$_2$dppf 1,1'-bis(diphenylphosphino) ferrocene palladium (II) dichloride
Pd(dtbpf)Cl$_2$ (1,1'-bis(di-t-butylphosphino)ferrocene palladium dichloride
Pd$_2$(dba)$_3$ tris(dibenzylideneacetone)dipalladium(0)
Pd(OAc)$_2$ palladium(II) acetate
P(Cy)$_3$ tricyclohexylphosphine
t-Bu$_3$P tri-t-butylphosphine
PPh$_3$ triphenylphosphine
PrOH propanol
i-PrOH iso-propanol
Pt/C platinum on carbon
t-BuOK potassium tert-butoxide
rt room temperature
Rt Retention time
sat saturated
SiO$_2$ silica
TFA trifluoroacetic acid
THF tetrahydrofuran
TLC thin layer chromatography
TMS trimethylsilyl Preparatory Details

EXAMPLE 1

(S)-2-Amino-N-[(4-fluoro-3-{1-[1-(2-methoxy-ethyl)-4-(morpholine-4-carbonyl)-1H-indole-3-carbonyl]-piperidin-4-yl}-benzylcarbamoyl)-methyl]-3-methyl-butyramide hydrochloride

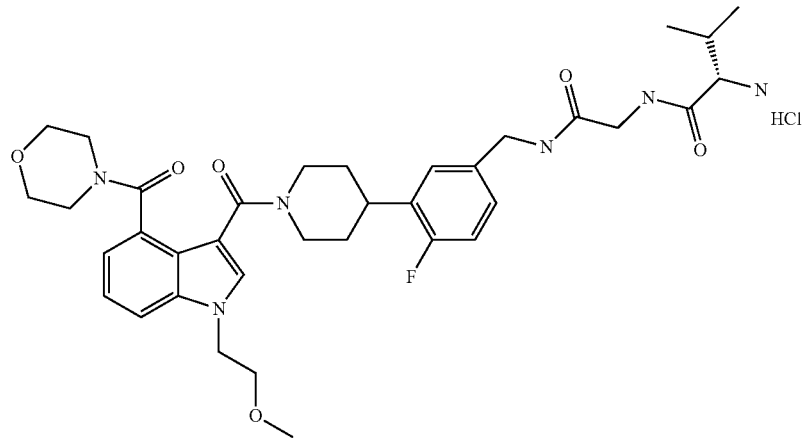 [SMILES: COCCn1cc(C(=O)N2CCC(c3cc(CNC(=O)CNC(=O)[C@@H](N)C(C)C)ccc3F)CC2)c2c(C(=O)N3CCOCC3)cccc21 ; Cl]

1A. ((S)-1-{[(4-Fluoro-3-{1-[1-(2-methoxy-ethyl)-4-(morpholine-4-carbonyl)-1H-indole-3-carbonyl]-piperidin-4-yl}-benzylcarbamoyl)-methyl]-carbamoyl}-2-methyl-propyl)-carbamic acid tert-butyl ester

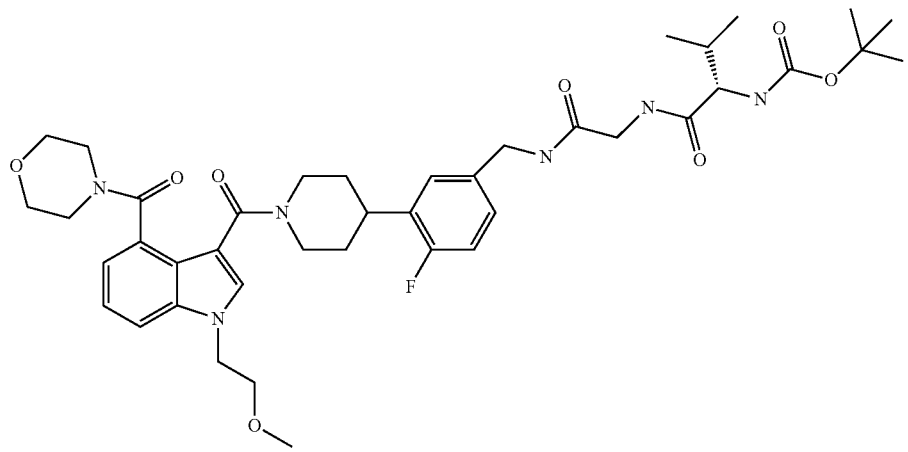 [SMILES: COCCn1cc(C(=O)N2CCC(c3cc(CNC(=O)CNC(=O)[C@@H](NC(=O)OC(C)(C)C)C(C)C)ccc3F)CC2)c2c(C(=O)N3CCOCC3)cccc21]

[4-(5-Aminomethyl-2-fluoro-phenyl)-piperidin-1-yl]-[1-(2-methoxy-ethyl)-4-(morpholine-4-carbonyl)-1H-indol-3-yl]-methanone hydrochloride (100 mg, 0.18 mmol) was dissolved in DMF (2.6 mL) under nitrogen and stirred at 0° C. for 5 min. To this was added sequentially hydroxybenzotriazole (77 mg, 0.57 mmol), BOC-Val-Gly-OH (59 mg, 0.21 mmol), triethylamine (0.05 mL, 0.36 mmol) followed by 1-(3-dimethylaminopropyl)-3-ethylcarbodiimide hydrochloride (41 mg, 0.21 mmol). The reaction mixture was warmed to room temperature and stirred overnight. The reaction mixture was diluted with ethyl acetate (30 mL) and washed with brine (30 mL). The brine was back extracted with ethyl acetate (2×30 mL) and the organic fractions were combined and washed with 10% citric acid (2×30 mL), sat sodium bicarbonate solution (2×30 mL) and brine (30 mL). The organic layer was dried over sodium sulfate, filtered and concentrated in vacuo to give the crude product which was purified by $SiO_2$ column chromatography using 5% MeOH/$CH_2Cl_2$ as the eluent to afford (1-{[(4-fluoro-3-{1-[1-(2-methoxy-ethyl)-4-(morpholine-4-carbonyl)-1H-indole-3-carbonyl]-piperidin-4-yl}-benzylcarbamoyl)-methyl]-carbamoyl}-2-methyl-propyl)-carbamic acid tert-butyl ester (100 mg, 72%). $^1$H NMR (300 MHz, $CDCl_3$) δ 7.40-7.30 (m, 2H), 7.28-7.21 (m, 2H), 7.18-7.10 (m, 1H), 7.08-7.00 (m, 1H), 6.98-6.85 (m, 1H), 5.00-4.90 (br s, 1H), 4.30 (t, 2H), 3.85-3.70 (br m, 2H), 3.73 (t, 2H), 3.47 (s, 2H), 3.33 (s, 3H), 3.20-2.90 (br m, 2H), 1.90-1.60 (br m, 6H), 1.30-1.24 (m, 10H), 1.80-1.70 (br m, 6H); $^{19}$F NMR (282 MHz, $CDCl_3$) δ −57.60 (s, 1F); MS m/z: [M+H]$^+$=779.

1. (S)-2-Amino-N-[(4-fluoro-3-{1-[1-(2-methoxy-ethyl)-4-(morpholine-4-carbonyl)-1H-indole-3-carbonyl]-piperidin-4-yl}-benzylcarbamoyl)-methyl]-3-methyl-butyramide hydrochloride 4N HCl in dioxane (2.5 mL) was added to ((S)-1-{[(4-fluoro-3-{1-[1-(2-methoxy-ethyl)-4-(morpholine-4-carbonyl)-1H-indole-3-carbonyl]-piperidin-4-yl}-benzylcarbamoyl)-methyl]-carbamoyl}-2-methyl-propyl)-carbamic acid tert-butyl ester (0.94 mg, 0.12 mmol). The resulting colorless solution was stirred under $N_2$ at rt overnight. The reaction mixture was concentrated in vacuo and the residue was triturated with $Et_2O$ (10 mL). The ethereal layer was removed and the pale yellow solid washed with $Et_2O$ (3×10 mL). The solid was dried under vacuum to afford the product (85 mg, 99%). $^1$H NMR (300 MHz, DMSO-$d_6$) δ 8.74-8.71 (m, 1H), 8.54-8.51 (m, 1H), 8.20 (br s, 2H), 7.7.63-7.60 (m, 1H), 7.44-7.36 (m, 1H), 7.32-7.21 (m, 1H), 7.13-7.05 (m, 1H), 7.01-6.98 (d, 1H), 4.39 (t, 2H), 4.25 (d, 2H), 4.21-4.15 (m, 1H), 3.88-3.83 (m, 2H), 3.79-3.77 (m, 1H), 3.69 (t, 2H), 3.62 (br s, 2H), 3.24 (s, 3H), 3.08-2.88 (m, 2H), 2.10-2.03 (m, 1H), 1.85-1.60 (m, 6H), 1.11-1.07 (m, 1H), 0.94 (d, 6H); MS m/z: [M+H]$^+$=679.

EXAMPLE 2

(S)-2-Amino-N-(4-fluoro-3-{1-[1-(2-methoxy-ethyl)-4-(morpholine-4-carbonyl)-1H-indole-3-carbonyl]-piperidin-4-yl}-benzyl)-3-methyl-butyramide hydrochloride

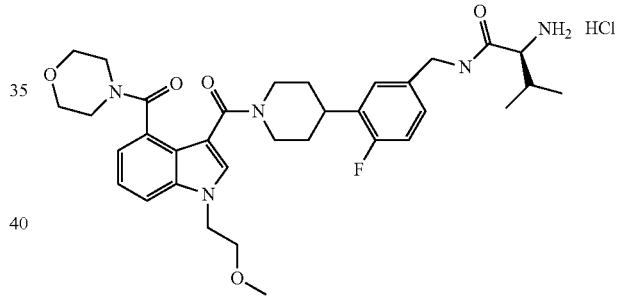

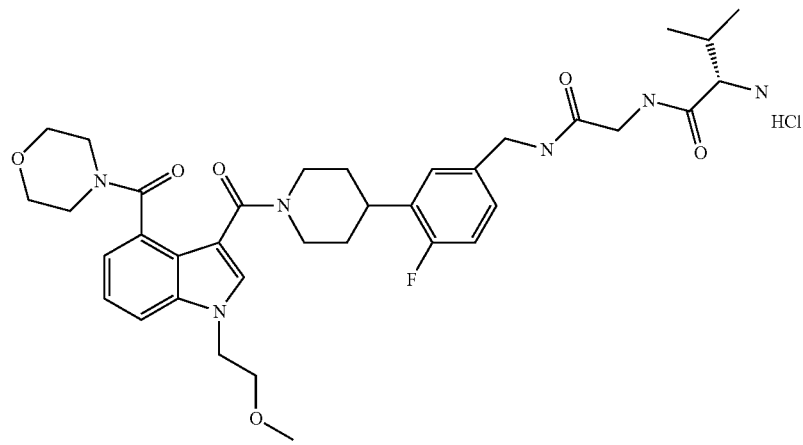 [SMILES: COCCn1cc(C(=O)N2CCC(c3cc(CNC(=O)CNC(=O)[C@@H](N)C(C)C)ccc3F)CC2)c2c(C(=O)N3CCOCC3)cccc21 ; Cl]

2A. [(S)-1-(4-Fluoro-3-{1-[1-(2-methoxy-ethyl)-4-(morpholine-4-carbonyl)-1H-indole-3-carbonyl]-piperidin-4-yl}-benzylcarbamoyl)-2-methyl-propyl]-carbamic acid tert-butyl ester

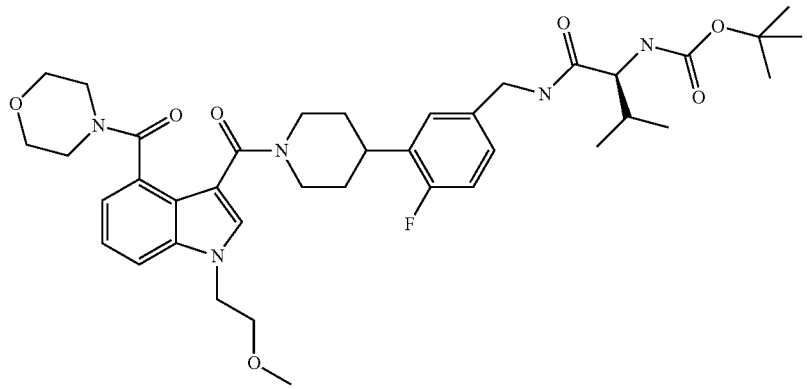 [SMILES: COCCn1cc(C(=O)N2CCC(c3cc(CNC(=O)[C@@H](NC(=O)OC(C)(C)C)C(C)C)ccc3F)CC2)c2c(C(=O)N3CCOCC3)cccc21]

The title compound was prepared in a similar manner as in Example 1A using BOC-L-Val-OH as the starting material. $^1$H NMR (300 MHz, CDCl$_3$) δ 7.41-7.33 (m, 2H), 7.25-7.21 (m, 2H), 7.15 (d, 1H), 7.12-7.02 (m, 1H), 6.98-6.91 (m, 1H), 6.45 (br s, 1H), 4.40 (br s, 2H), 4.30 (t, 2H), 3.94-3.86 (m, 1H), 3.80 (br s, 2H), 3.72 (t, 3H), 3.33 (s, 3H), 3.19-2.95 (m, 2H), 2.20-2.11 (m, 1H), 1.81-1.68 (m, 6H), 1.59 (s, 9H), 1.27-1.24 (m, 1H), 0.94-0.84 (m, 6H); MS m/z: [M+H]$^+$=722.

2 (S)-2-Amino-N-(4-fluoro-3-{1-[1-(2-methoxy-ethyl)-4-(morpholine-4-carbonyl)-1H-indole-3-carbonyl]-piperidin-4-yl}-benzyl)-3-methyl-butyramide hydrochloride

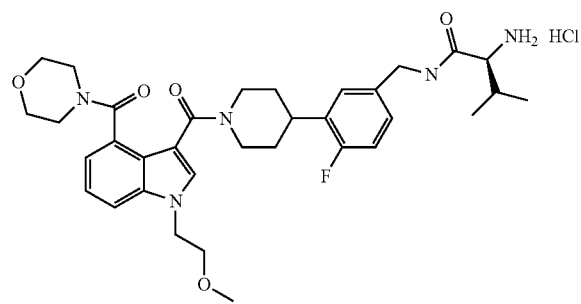 [SMILES: COCCn1cc(C(=O)N2CCC(c3cc(CNC(=O)[C@@H](N)C(C)C)ccc3F)CC2)c2c(C(=O)N3CCOCC3)cccc21 ; Cl]

The title compound was prepared in a similar manner as in Example 1B using [(S)-1-(4-fluoro-3-{1-[1-(2-methoxy-ethyl)-4-(morpholine-4-carbonyl)-1H-indole-3-carbonyl]-piperidin-4-yl}-benzylcarbamoyl)-2-methyl-propyl]-carbamic acid tert-butyl ester (0.134 mg, 0.18 mmol) as the starting material. $^1$H NMR (300 MHz, DMSO-d$_6$) δ 8.90 (br s, 1H), 8.14 (br s, 2H), 7.57 (s, 1H), 7.35 (d, 1H), 7.22-7.08 (m, 4H), 6.96 (d, 1H), 4.42-4.17 (m, 4H), 3.75-3.62 (m, 4H), 3.56-3.52 (m, 4H), 3.20 (s, 3H), 3.09-2.89 (m, 4H), 2.09-1.98 (m, 2H), 1.76-1.58 (m, 6H), 1.05 (t, 1H), 0.87 (d, 6H); MS m/z: [M+H]$^+$=622.

EXAMPLE 3

(R)-2-Amino-N-(4-fluoro-3-{1-[1-(2-methoxy-ethyl)-4-(morpholine-4-carbonyl)-1H-indole-3-carbonyl]-piperidin-4-yl}-benzyl)-3-methyl-butyramide hydrochloride

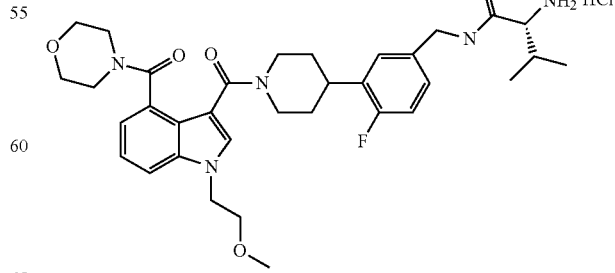

3A. [(R)-1-(4-Fluoro-3-{1-[1-(2-methoxy-ethyl)-4-(morpholine-4-carbonyl)-1H-indole-3-carbonyl]-piperidin-4-yl}-benzylcarbamoyl)-2-methyl-propyl]-carbamic acid tert-butyl ester

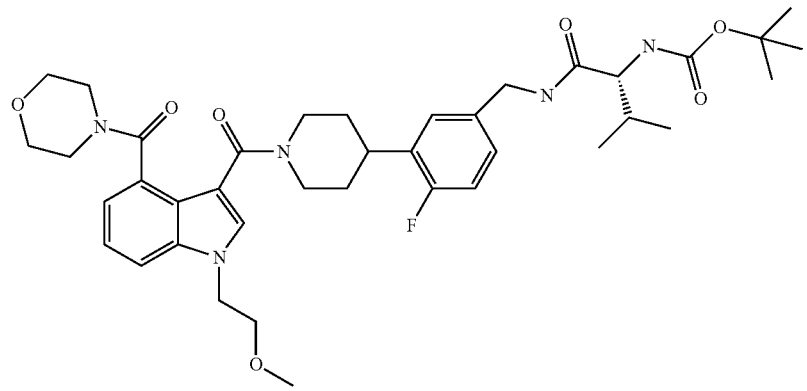 [SMILES: COCCn1cc(C(=O)N2CCC(c3cc(CNC(=O)[C@H](NC(=O)OC(C)(C)C)C(C)C)ccc3F)CC2)c2c(C(=O)N3CCOCC3)cccc21]

The title compound was prepared in a similar manner as in Example 1A using BOC-D-Val-OH as the starting material. ¹H NMR (300 MHz, CDCl₃) δ 7.42-7.36 (m, 2H), 7.30-7.25 (m, 2H), 7.15 (d, 1H), 7.09-7.03 (m, 1H), 6.96-6.91 (m, 1H), 6.56 (br s, 1H), 4.39 (br s, 2H), 4.29 (t, 2H), 3.93-3.88 (m, 1H), 3.80 (br s, 2H), 3.72 (t, 2H), 3.32 (s, 3H), 3.16-3.05 (m, 2H), 2.19-2.10 (m, 1H), 1.89-1.69 (m, 6H), 1.40 (s, 9H), 1.28-1.23 (m, 1H), 0.92-0.84 (m, 6H); MS m/z: [M+H]⁺ =722.

3. (R)-2-Amino-N-(4-fluoro-3-{1-[1-(2-methoxy-ethyl)-4-(morpholine-4-carbonyl)-1H-indole-3-carbonyl]-piperidin-4-yl}-benzyl)-3-methyl-butyramide hydrochloride

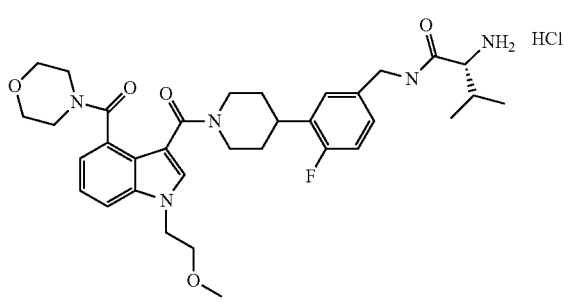 [SMILES: COCCn1cc(C(=O)N2CCC(c3cc(CNC(=O)[C@H](N)C(C)C)ccc3F)CC2)c2c(C(=O)N3CCOCC3)cccc21 ; Cl]

The title compound was prepared in a similar manner as in Example 1B using [(R)-1-(4-fluoro-3-{1-[1-(2-methoxy-ethyl)-4-(morpholine-4-carbonyl)-1H-indole-3-carbonyl]-piperidin-4-yl}-benzylcarbamoyl)-2-methyl-propyl]-carbamic acid tert-butyl ester as the starting material. ¹H NMR (300 MHz, DMSO-d₆) δ 8.89 (br s, 1H), 8.14 (br s, 2H), 7.61 (s, 1H), 7.38 (d, 1H), 7.30-7.12 (m, 4H), 7.00 (d, 1H), 4.41-4.19 (m, 4H), 3.71-3.65 (m, 4H), 3.63-3.55 (m, 4H), 3.23 (s, 3H), 3.12-2.95 (m, 4H), 2.12-2.03 (m, 2H), 1.77-1.61 (m, 6H), 1.09 (t, 1H), 0.91 (d, 6H); MS m/z: [M+H]⁺=622.

EXAMPLE 4

(S)-2-Amino-N-(4-fluoro-3-{1-[7-fluoro-1-(2-methoxy-ethyl)-4-trifluoromethoxy-1H-indole-3-carbonyl]-piperidin-4-yl}-benzyl)-3-methyl-butyramide hydrochloride Chiral

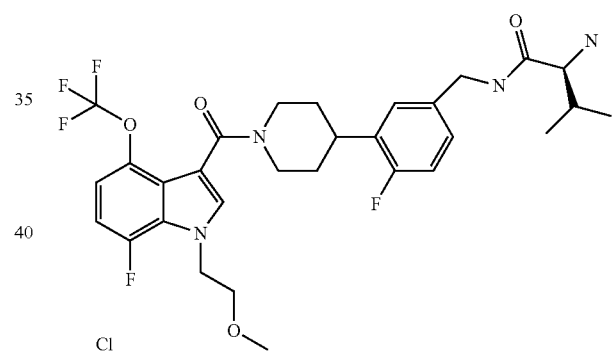

4A. [(S)-1-(4-Fluoro-3-{1-[7-fluoro-1-(2-methoxy-ethyl)-4-trifluoromethoxy-1H-indole-3-carbonyl]-piperidin-4-yl}-benzylcarbamoyl)-2-methyl-propyl]-carbamic acid tert-butyl ester Chiral

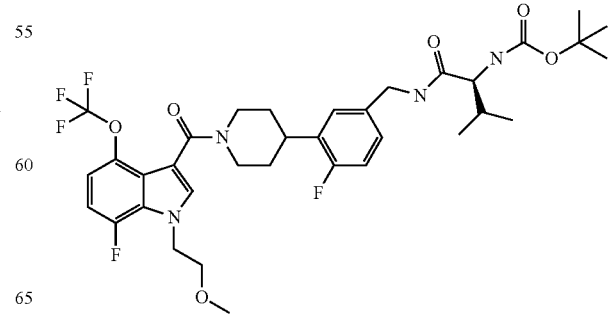

A solution of [4-(5-aminomethyl-2-fluoro-phenyl)-piperidin-1-yl]-[7-fluoro-1-(2-methoxy-ethyl)-4-trifluoromethoxy-1H-indol-3-yl]-methanone hydrochloride (0.3 g, 0.55 mmol), BOC-Val-OH (0.143 g, 0.66 mmol), EDCI (0.126 g, 0.66 mmol), HOBT (0.224 g, 1.65 mmol), and Et₃N (0.23 ml, 1.65 mmol) in CH₂Cl₂ (30 mL) was stirred at rt overnight. The reaction mixture was poured into EtOAc and the organic layer washed with 10% citric acid and brine. The organic layer was dried over MgSO₄, filtered and concentrated in vacuo to give the crude product. Purification by flash chromatography on SiO₂ eluting with 3% MeOH/CH₂Cl₂ afforded the desired product (0.39 g, 99%). ¹H NMR (300 MHz, CDCl₃) δ 7.4 (s, 1H), 7.1 (m, 2H), 7.0-6.8 (m, 3H), 6.3 (bs, 1H), 5.0 (bs, 1H), 4.5-4.3 (m, 4H), 3.9 (m, 1H), 3.8 (m, 2H), 3.35 (s, 3H), 3.1 (m, 2H), 2.2 (m, 2H), 2.0-1.6 (m, 6H), 1.4 (s, 9H), 0.9 (m, 6H). MS m/z: [M+H]⁺=711.

4. (S)-2-Amino-N-(4-fluoro-3-{1-[7-fluoro-1-(2-methoxy-ethyl)-4-trifluoromethoxy-1H-indole-3-carbonyl]-piperidin-4-yl}-benzyl)-3-methyl-butyramide hydrochloride

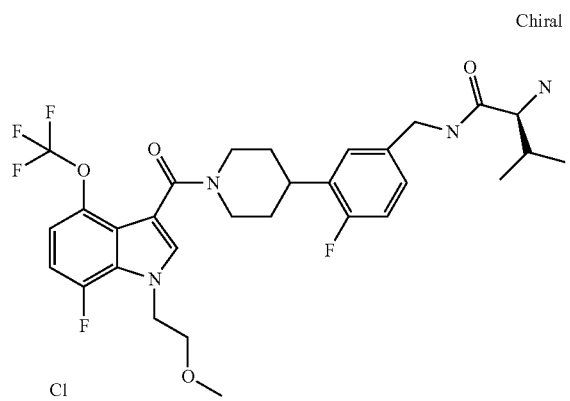 [SMILES: "Chiral" ; COCCn1cc(C(=O)N2CCC(c3cc(CNC(=O)[C@@H](N)C(C)C)ccc3F)CC2)c2c(OC(F)(F)F)ccc(F)c21 ; Cl]

To a solution of [(S)-1-(4-fluoro-3-{1-[7-fluoro-1-(2-methoxy-ethyl)- 4-trifluoromethoxy-1H-indole-3-carbonyl]-piperidin-4-yl}-benzylcarbamoyl)-2-methyl-propyl]-carbamic acid tert-butyl ester (0.35 g, 0.49 mmol) in ether (20 mL) was added 2M HCl in ether (10 mL, 20.0 mmol). The reaction mixture was stirred at rt overnight. The resulting precipitate was collected to give the titled compound (260 mg, 82%). ¹H NMR (300 MHz, DMSO-d₆) δ 9.0 (m, 1H), 8.3 (bs, 2H), 7.7 (s, 1H), 7.3-7.0 (m, 5H), 4.5 (m, 2H), 4.4-4.2 (m, 2H), 3.7-3.5 (m, 6H), 3.2 (s, 3H), 3.1-2.9 (m, 2H), 2.1 (m, 1H), 1.85-1.5 (m, 4H), 0.9 (m, 6H). MS m/z: [M+H]⁺=611.

EXAMPLE 5

(S)-2-Amino-N-[(4-fluoro-3-{1-[7-fluoro-1-(2-methoxy-ethyl)-4-trifluoromethoxy-1H-indole-3-carbonyl]-piperidin-4-}-benzylcarbamoyl)-methyl]-3-methyl-butyramide hydrochloride

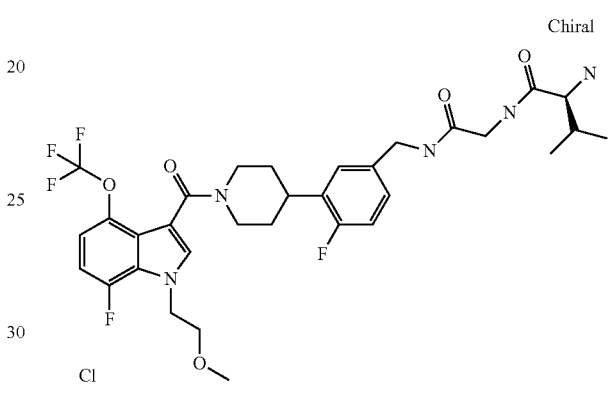

5A. ((S)-1-{[(4-Fluoro-3-{1-[7-fluoro-1-(2-methoxy-ethyl)-4-trifluoromethoxy-1H-indole-3-carbonyl]-piperidin-4-yl}-benzylcarbamoyl)-methyl]-carbamoyl}-2-methyl-propyl)-carbamic acid tert-butyl ester

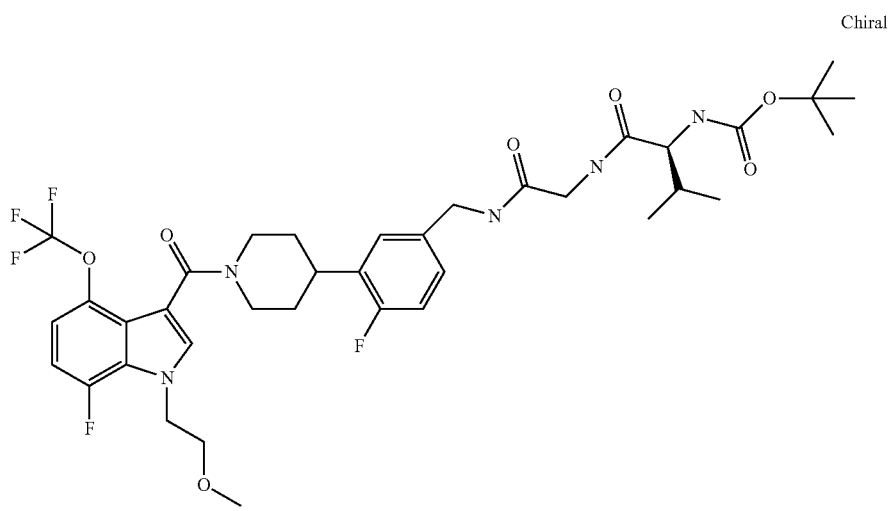

A solution of [4-(5-aminomethyl-2-fluoro-phenyl)-piperidin-1-yl]-[7-fluoro-1-(2-methoxy-ethyl)-4-trifluoromethoxy-1H-indol-3-yl]-methanone hydrochloride (0.3 g, 0.55 mmol), BOC-Val-GlyOH (0.18 g, 0.66 mmol), EDCI (0.126 g, 0.66 mmol), HOBT (0.224 g, 1.65 mmol), and Et$_3$N (0.23 ml, 1.65 mmol) in DMF (15 mL) was stirred at room temperature overnight. The reaction mixture was poured into EtOAc and the organic layer washed with water and brine. The organic layer was dried over MgSO$_4$, filtered and concentrated in vacuo to give the crude product. Purification by flash chromatography on SiO$_2$ eluting with 3% MeOH/CH$_2$Cl$_2$ provided the desired product (0.4 g, 95%). $^1$H NMR (300 MHz, CDCl$_3$) δ 7.4 (s, 1H), 7.1 (m, 2H), 7.0-6.8 (m, 3H), 6.7 (bs, 1H), 5.1 (bs, 1H), 4.5-4.3 (m, 4H), 4.1-3.7 (m, 6H), 3.35 (s, 3H), 3.1 (m, 3H), 2.1 (m, 1H), 1.8-1.6 (m, 6H), 1.4 (s, 9H), 0.9 (m, 6H). MS m/z: [M+H]$^+$=768.

5. (S)-2-Amino-N-[(4-fluoro-3-{1-[7-fluoro-1-(2-methoxy-ethyl)-4-trifluoromethoxy-1H-indole-3-carbonyl]-piperidin-4-yl}-benzylcarbamoyl)-methyl]-3-methyl-butyramide hydrochloride

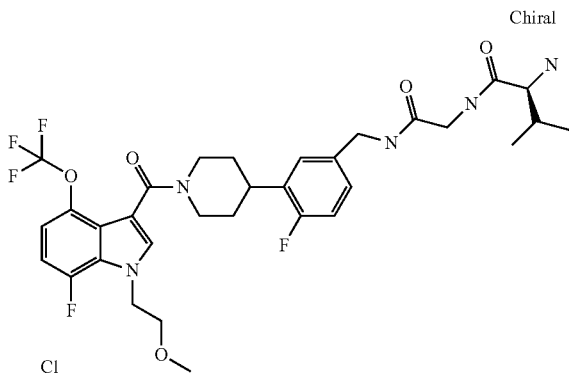

The title compound was prepared in a similar manner as in Example 4B using ((S)-1-{[(4-fluoro-3-{1-[7-fluoro-1-(2-methoxy-ethyl)-4-trifluoromethoxy-1H-indole-3-carbonyl]-piperidin-4-yl}-benzylcarbamoyl)-methyl]-carbamoyl}-2-methyl-propyl)-carbamic acid tert-butyl ester as the starting material. $^1$H NMR (300 MHz, DMSO-d$_6$) δ 8.8 (m, 1H), 8.6 (m, 1H), 8.3 (bs, 2H), 7.7 (s, 1H), 7.3-7.0 (m, 5H), 4.5 (m, 2H), 4.3 (t, 2H), 3.8 (t, 2H), 3.7-3.5 (m, 6H), 3.2 (s, 3H), 3.0 (m, 2H), 2.1 (m, 1H), 1.8-1.5 (m, 4H), 0.9 (m, 6H). MS m/z: [M+H]$^+$=668.

EXAMPLE 6

(R)-2-Amino-N-(4-fluoro-3-{1-[7-fluoro-1-(2-methoxy-ethyl)-4-trifluoromethoxy-1H-indole-3-carbonyl]-piperidin-4-yl}-benzyl)-3-methyl-butyramide hydrochloride

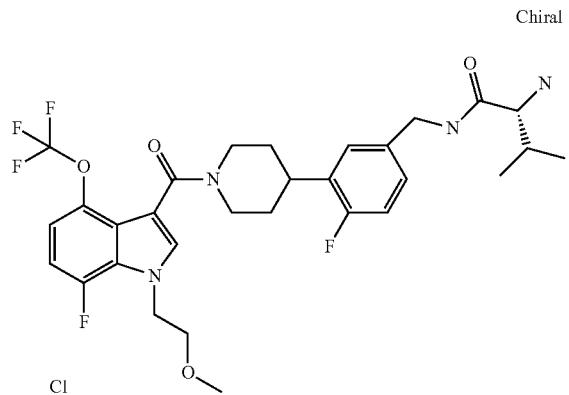 [SMILES: "Chiral" ; COCCn1cc(C(=O)N2CCC(c3cc(CNC(=O)[C@H](N)C(C)C)ccc3F)CC2)c2c(OC(F)(F)F)ccc(F)c21 ; Cl]

6A. [(R)-1-(4-Fluoro-3-{1-[7-fluoro-1-(2-methoxy-ethyl)-4-trifluoromethoxy-1H-indole-3-carbonyl]-piperidin-4-yl}-benzylcarbamoyl)-2-methyl-propyl]-carbamic acid tert-butyl ester

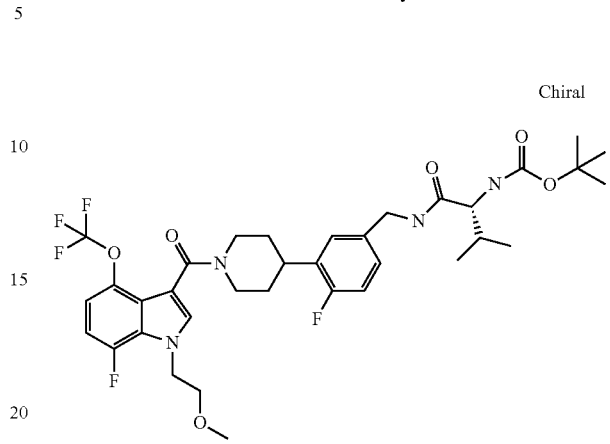

The title compound was prepared in a similar manner as in Example 5A using D-BOC-Val-OH as the starting material. $^1$H NMR (300 MHz, CDCl$_3$) δ 7.4 (s, 1H), 7.1 (m, 2H), 7.0-6.8 (m, 3H), 6.3 (bs, 1H), 5.0 (bs, 1H), 4.5-4.3 (m, 4H), 3.9 (m, 1H), 3.8 (m, 2H), 3.35 (s, 3H), 3.1 (m, 2H), 2.2 (m, 2H), 2.0-1.6 (m, 6H), 1.4 (s, 9H), 0.9 (m, 6H). MS m/z: [M+H]$^+$=711.

6. (R)-2-Amino-N-(4-fluoro-3-{1-[7-fluoro-1-(2-methoxy-ethyl)-4-trifluoromethoxy-1H-indole-3-carbonyl]-piperidin-4-yl}-benzyl)-3-methyl-butyramide hydrochloride

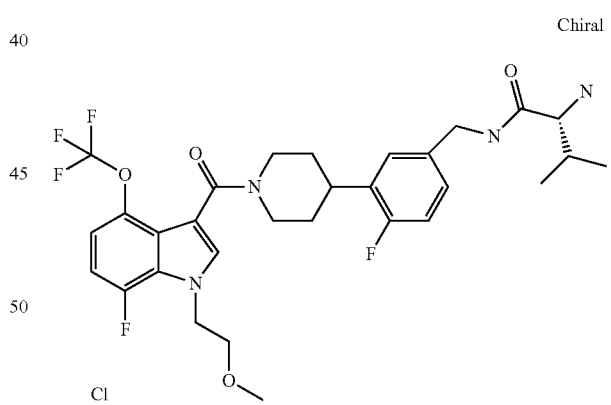

The title compound was prepared in a similar manner as in Example 4B using [(R)-1-(4-fluoro-3-{1-[7-fluoro-1-(2-methoxy-ethyl)-4-trifluoromethoxy-1H-indole-3-carbonyl]-piperidin-4-yl}-benzylcarbamoyl)-2-methyl-propyl]-carbamic acid tert-butyl ester as the starting material. $^1$H NMR (300 MHz, DMSO-d$_6$) δ 9.0 (m, 1H), 8.3 (bs, 2H), 7.7 (s, 1H), 7.3-7.0 (m, 5H), 4.5 (m, 2H), 4.4-4.2 (m, 2H), 3.7-3.5 (m, 6H), 3.2 (s, 3H), 3.1-2.9 (m, 2H), 2.1 (m, 1H), 1.85-1.5 (m, 4H), 0.9 (m, 6H). MS m/z: [M+H]$^+$=611.

EXAMPLE 7

(S)-2-Amino-N—[(S)-1-(4-fluoro-3-{1-[7-fluoro-1-(2-methoxy-ethyl)-4-trifluoromethoxy-1H-indole-3-carbonyl]-piperidin-4-yl}-benzylcarbamoyl)-2-methyl-propyl]-3-methyl-butyramide hydrochloride 7. (S)-2-Amino-N—[(S)-1-(4-fluoro-3-{1-[7-fluoro-1-(2-methoxy-ethyl)-4-trifluoromethoxy-1H-indole-3-carbonyl]-piperidin-4-yl}-benzylcarbamoyl)-2-methyl-propyl]-3-methyl-butyramide hydrochloride

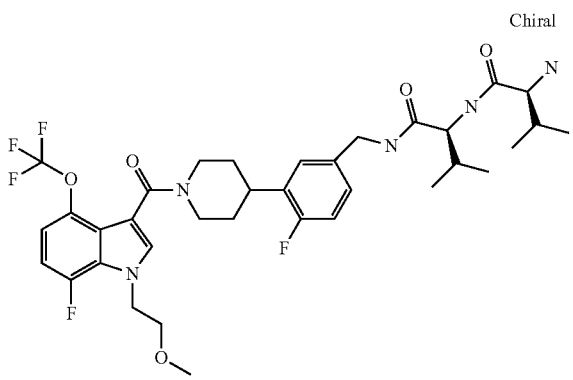

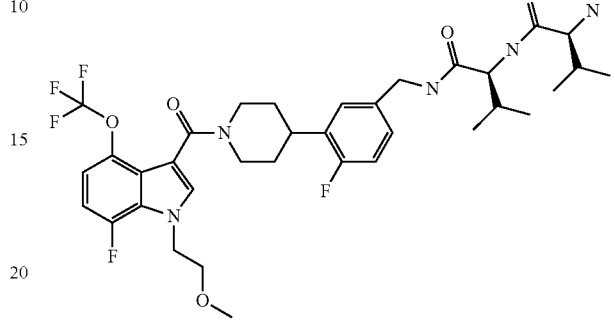

7A. {(S)-1-[(S)-1-(4-Fluoro-3-{1-[7-fluoro-1-(2-methoxy-ethyl)-4-trifluoromethoxy-1H-indole-3-carbonyl]-piperidin-4-yl}-benzylcarbamoyl)-2-methyl-propylcarbamoyl]-2-methyl-propyl}-carbamic acid tert-butyl ester The title compound was prepared in a similar manner as in Example 4B using {(S)-1-[(S)-1-(4-fluoro-3-{1-[7-fluoro-1-(2-methoxy-ethyl)-4-trifluoromethoxy-1H-indole-3-carbonyl]-piperidin-4-yl}-benzylcarbamoyl)-2-methyl-propylcarbamoyl]-2-methyl-propyl}-carbamic acid tert-butyl ester as the starting material. $^1$H NMR (300 MHz, DMSO-d$_6$) δ 8.7 (m, 1H), 8.5 (d, 1H), 8.2 (m, 3H), 7.7 (s, 1H), 7.3-7.0 (m, 5H),

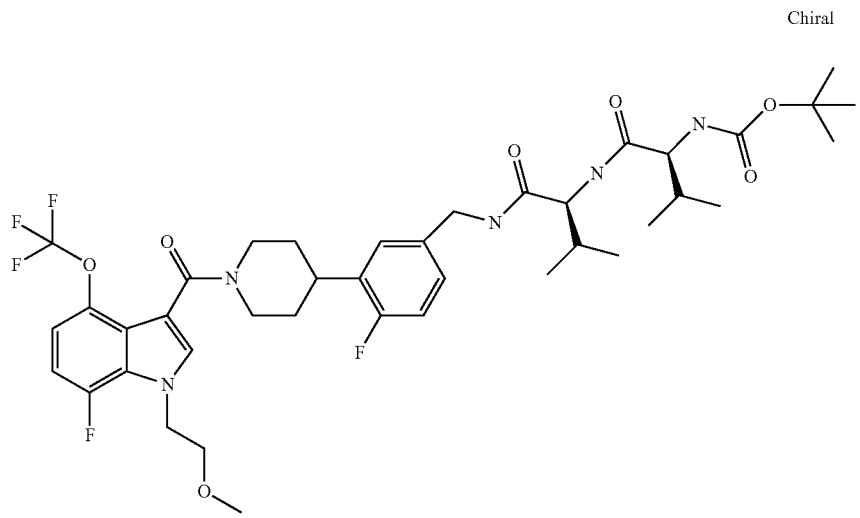 [SMILES: "Chiral" ; COCCn1cc(C(=O)N2CCC(c3cc(CNC(=O)[C@@H](NC(=O)[C@@H](NC(=O)OC(C)(C)C)C(C)C)C(C)C)ccc3F)CC2)c2c(OC(F)(F)F)ccc(F)c21]

The title compound was prepared in a similar manner as in Example 5A using BOC-Val-Val-OH as the starting material. $^1$H NMR (300 MHz, CDCl$_3$) δ 7.4 (s, 1H), 7.2 (m, 2H), 6.9 (m, 3H), 6.7 (bs, 1H), 6.5 (bs, 1H), 5.0 (bs, 1H), 4.6-4.2 (m, 5H), 3.9 (m, 1H), 3.7 (m, 2H), 3.4 (s, 3H), 3.1 (m, 2H), 2.9 (m, 2H), 2.4-2.2 (m, 2H), 1.8-1.6 (m, 5H), 1.4 (s, 9H), 0.9 (m, 12H). MS m/z: [M+H]$^+$=810.

4.5 (m, 2H), 4.3 (m, 2H), 3.9-3.7 (m, 6H), 3.3 (s, 3H), 3.1 (m, 2H), 2.0 (m, 2H), 1.8-1.6 (m, 4H), 0.9 (m, 12H). MS m/z: [M+H]$^+$=710.

BIOLOGICAL ACTIVITY

The properties of the compound of the present invention are demonstrated by: 1) the parent's beta-Tryptase Inhibitory Potency (IC$_{50}$ and K$_i$ values) and 2) stability of the prodrug in rat plasma.

In Vitro Test Procedure

As all the actions of tryptase, as described in the background section, are dependent on its catalytic activity, then compounds that inhibit its catalytic activity will potentially inhibit the actions of tryptase. Inhibition of this catalytic activity may be measured by the in vitro enzyme assay and the cellular assay.

Tryptase inhibition activity is confirmed using either isolated human lung tryptase or recombinant human beta tryptase expressed in yeast cells. Essentially equivalent results are obtained using isolated native enzyme or the expressed enzyme. The assay procedure employs a 96 well microplate (Costar 3590) using L-pyroglutamyl-L-prolyl-L-arginine-para-nitroanilide (S2366: Quadratech) as substrate (essentially as described by McEuen et. al. Biochem Pharm, 1996, 52, pages 331-340). Assays are performed at room temperature using 0.5 mM substrate ($2\times K_m$) and the microplate is read on a microplate reader (Beckman Biomek Plate reader) at 405 nm wavelength.

Materials and Methods for Tryptase Primary Screen (Chromogenic Assay)

Assay Buffer 50 mM Tris (pH 8.2), 100 mM NaCl, 0.05% Tween 20, 50 µg/mL heparin.

Substrate

S2366 (Stock solutions of 2.5 mM).

Enzyme

Purified recombinant beta Tryptase Stocks of 310 µg/mL.
Protocol (Single Point Determination)
    Add 60 µL of diluted substrate (final concentration of 500 µM in assay buffer) to each well
    Add compound in duplicates, final concentration of 20 volume 20 µL
    Add enzyme at a final concentration of 50 ng/mL in a volume of 20 µL
    Total volume for each well is 100 µL
    Agitate briefly to mix and incubate at room temp in the dark for 30 minutes
    Read absorbencies at 405 nM
Each plate has the following controls:
Totals: 60 µL of substrate, 20 µL of buffer (with 0.2% final concentration of DMSO), 20 µL of enzyme
Non-specific: 60 µL of substrate, 40 µL of buffer (with 0.2% DMSO)
Totals: 60 µL of substrate, 20 µL of buffer (No DMSO), 20 µL of enzyme
Non-specific: 60 µL of substrate, 40 µL of buffer (No DMSO)
Protocol ($IC_{50}$ and $K_i$ Determination)

The protocol is essentially the same as above except that the compound is added in duplicates at the following final concentrations: 0.01, 0.03, 0.1, 0.3, 1, 3, 10 µM (All dilutions carried out manually). For every assay, whether single point or $IC_{50}$ determination, a standard compound is used to derive $IC_{50}$ for comparison. From the $IC_{50}$ value, the $K_i$ can be calculated using the following formula: $K_i = IC_{50}/(1+[\text{Substrate}]/K_m)$.

The beta-Tryptase inhibitory potency for the parent compounds of the prodrugs of formula I are:

TABLE 1

| Activity of parent drug against beta-Tryptase | |
|---|---|
| EXAMPLE | Tryptase Ki (nM) |
| Parent of 1 | 29 |
| Parent of 4 | 38 |

Plasma Stability

The rat plasma stability of Example 1 was tested by incubation of the compound in rat plasma at 100 ng/mL followed by LC-MS/MS bioanalysis to measure remaining parent compound relative to the time zero condition (no incubation). Concentrations of 1 remaining at 1 and 4 hr after incubation at 37° C. were 19% and 0%, indicating 1 was very unstable under these conditions. Since 1 was designed as a prodrug, plasma instability is a desirable attribute.

We claim:
1. A compound of formula (I):

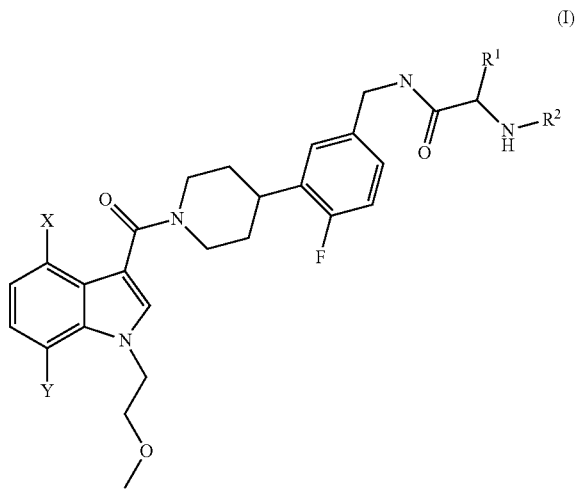

wherein,

X and Y are selected from the group consisting of hydrogen, methyl, fluoro, chloro, trifluoromethyl, methoxy, trifluoromethoxy, morpholin-4-yl-methanone such that not two of the substituents are hydrogen at the same time;

$R^1$ is H, lower alkyl or substituted alkyl;

$R^2$ is selected from the group consisting of hydrogen and natural and unnatural amino acids; or an N-oxide of said compound, a pharmaceutically acceptable salt of said compound, a solvate of said compound or a hydrate of said compound.

2. A compound according to claim 1 wherein $R^2$ is selected from the group consisting of hydrogen and —C(O)CH(CH(CH$_3$)$_2$)NH$_2$.

3. A compound according to claim 2 in which X is —OCF$_3$.

4. A compound according to claim 2 in which X is morpholin-4-yl-methanone.

5. A compound according to claim 1 in which $R^1$ is isopropyl.

6. A compound according to claim 1 which is selected from the group consisting of:
- (S)-2-Amino-N-[(4-fluoro-3-{1-[1-(2-methoxy-ethyl)-4-(morpholine-4-carbonyl)-1H-indole-3-carbonyl]-piperidin-4-yl}-benzylcarbamoyl)-methyl]-3-methyl-butyramide hydrochloride,
- (S)-2-Amino-N-(4-fluoro-3-{1-[1-(2-methoxy-ethyl)-4-(morpholine-4-carbonyl)-1H-indole-3-carbonyl]-piperidin-4-yl}-benzyl)-3-methyl-butyramide hydrochloride,
- (R)-2-Amino-N-(4-fluoro-3-{1-[1-(2-methoxy-ethyl)-4-(morpholine-4-carbonyl)-1H-indole-3-carbonyl]-piperidin-4-yl}-benzyl)-3-methyl-butyramide hydrochloride,
- (S)-2-Amino-N-(4-fluoro-3-{1-[7-fluoro-1-(2-methoxy-ethyl)-4-trifluoromethoxy-1H-indole-3-carbonyl]-piperidin-4-yl}-benzyl)-3-methyl-butyramide hydrochloride,
- (S)-2-Amino-N-[(4-fluoro-3-{1-[7-fluoro-1-(2-methoxy-ethyl)-4-trifluoromethoxy-1H-indole-3-carbonyl]-piperidin-4-yl}-benzylcarbamoyl)-methyl]-3-methyl-butyramide hydrochloride,
- (R)-2-Amino-N-(4-fluoro-3-{1-[7-fluoro-1-(2-methoxy-ethyl)-4-trifluoromethoxy-1H-indole-3-carbonyl]-piperidin-4-yl}-benzyl)-3-methyl-butyramide hydrochloride, and
- (S)-2-Amino-N—[(S)-1-(4-fluoro-3-{1-[7-fluoro-1-(2-methoxy-ethyl)-4-trifluoromethoxy-1H-indole-3-carbonyl]-piperidin-4-yl}-benzylcarbamoyl)-2-methyl-propyl]-3-methyl-butyramide hydrochloride.

7. A pharmaceutical composition comprising a compound according to claim 1 in a pharmaceutically acceptable carrier.

\* \* \* \* \*